(12) United States Patent
McGuigan et al.

(10) Patent No.: US 8,473,311 B2
(45) Date of Patent: Jun. 25, 2013

(54) COMPUTER SYSTEM AND METHOD FOR GENERATING HEALTHCARE RISK INDICES USING MEDICAL CLAIMS INFORMATION

(75) Inventors: Kimberly A. McGuigan, Ridgewood, NJ (US); Debra A. Maldonato, Chestnut Ridge, NY (US); Qingshan Qian, Los Angeles, CA (US); Jianying Yao, Allendale, NJ (US)

(73) Assignee: Medco Health Solutions, Inc., Franklin Lakes, NJ (US)

( * ) Notice: Subject to any disclaimer, the term of this patent is extended or adjusted under 35 U.S.C. 154(b) by 1438 days.

(21) Appl. No.: 10/912,133

(22) Filed: Aug. 6, 2004

(65) Prior Publication Data

US 2005/0091084 A1    Apr. 28, 2005

Related U.S. Application Data

(63) Continuation-in-part of application No. 10/689,852, filed on Oct. 22, 2003.

(51) Int. Cl.
*G06Q 50/00*        (2012.01)

(52) U.S. Cl.
USPC ............................... 705/3; 705/2; 705/4

(58) Field of Classification Search
USPC ............ 705/2–4; 600/523; 378/54; 435/6.11
See application file for complete search history.

(56) References Cited

U.S. PATENT DOCUMENTS

| | | | |
|---|---|---|---|
| 4,667,292 A | 5/1987 | Mohlenbrock et al. | |
| 5,018,067 A | 5/1991 | Mohlenbrock et al. | |
| 5,325,293 A | 6/1994 | Dorne | |
| 7,319,970 B1 * | 1/2008 | Simone | 705/4 |
| 7,444,291 B1 * | 10/2008 | Prasad et al. | 705/2 |
| 2003/0198316 A1 * | 10/2003 | Dewaele et al. | 378/54 |
| 2004/0076988 A1 * | 4/2004 | Taylor et al. | 435/6 |

* cited by examiner

*Primary Examiner* — Valerie Lubin
(74) *Attorney, Agent, or Firm* — Husch Blackwell LLP

(57) ABSTRACT

A healthcare risk index is generated using a patient or individual's medical claims. The index may be used to explain and predict variation in pharmacy-related costs and variation in total healthcare costs or utilization. In particular, one example of such a method involves first generating a medical condition score using the individual's medical information for each medical condition possessed by the individual. From there, each medical condition score is modified according to a regression coefficient, to result in one or more modified medical condition scores. Finally, the risk index may be generated by summing the medical condition scores. This risk index is indicative of at least one of the individual's medical costs, chronic medical conditions, and variation in medical costs.

12 Claims, 5 Drawing Sheets

| CONDITIONS (3-DIGIT ICD-9 CODES) | WEIGHTS |
|---|---|
| ('001','002','003','004','005','006','007','008','009') | 0.51927 |
| ('010','011','012','013','014','015','016','017','018') | 0.67509 |
| ('020','021','022','023','024','025','026','027') | 0.08939 |
| ('030','031','032','033','034','035','036','037','038','039') | 0.62525 |
| ('042') | 2.69484 |
| ('040','041','043','044','045','046','047','048','049') | 0.41242 |
| ('060','061','062','063','064','065','066') | 0.80152 |
| ('080','081','082','083','084','085','086','087','088') | 0.71995 |
| ('090','091','092','093','094','095','096','097','098','099') | 0.75938 |
| ('100','101','102','103','104') | 0.52743 |
| ('112') | 0.32795 |
| ('110','111','113','114','115','116','117','118') | 0.40347 |
| ('120','121','122','123','124','125','126','127','128','129') | 0.44208 |
| ('130','131','132','133','134','135','136') | 0.35877 |
| ('140','141','142','143','144','145','146','147','148','149') | 0.24868 |
| ('150','151','152','153','154','155','156','157','158','159') | 0.63380 |
| ('160','161','162','163','164','165') | 0.27897 |
| ('170','171','182','173','174','175','176') | 0.57732 |
| ('179','180','181','182','183','184','185','186','187','188','189') | 0.89246 |
| ('190','191','192','193','194','195','196','197','198','199') | 0.52960 |
| ('200','201','202','203','203','205','206','207','208') | 0.81431 |
| ('210','211','212','213','214','215','216','217','218','219','220','221','222','223','224','225','226','227','228','229') | 0.74376 |
| ('230','231','232','233','234') | 0.32539 |
| ('235','236','237','238') | 0.41101 |
| ('239') | 0.28258 |
| ('240','241','242','243','244','245','246') | 0.67404 |
| ('250') | 1.14089 |
| ('251','251','252','253','254','255','256','257','258','259') | 0.62899 |
| ('260','261','262','263','264','265','266','267','268','269') | 0.08597 |
| ('272') | 0.90419 |
| ('270','271','273','274','275','276','277','278','279') | 0.43509 |
| ('280','281','282','283','284','285','286','287','288','288') | 0.47204 |
| ('290','291','292','293','294') | 0.24155 |
| ('296') | 0.64358 |
| ('295','297','298','299') | 0.84728 |
| ('300') | 0.80920 |
| ('301','303','304','305','307','309','310','311','312','313','314','315','316') | 0.90559 |
| ('317','318','319') | 0.63410 |
| ('320','321','322','323','324','325','326') | 0.35817 |
| ('330','331','332','333','334','335','336','337') | 0.25770 |
| ('340','341','342','343','344','345','346','347','348','349') | 0.51194 |
| ('350','351','352','353','354','355','356','357','358','359') | 0.30996 |
| ('362') | 0.49639 |
| ('365') | 0.56865 |
| ('366') | 0.43326 |
| ('372') | 0.58989 |
| ('360','361','363','364','367','368','369','370','371','373','374','375','376','377','378','379') | 0.73834 |
| ('381') | 0.55835 |
| ('382') | 0.89834 |
| ('383') | 0.44642 |
| ('384','385','386','387','388','389') | 0.38326 |
| ('390','391','392') | 0.75715 |
| ('393','394','395','396','397','398') | 0.37887 |
| ('401','402','403','404','405') | 1.07218 |

FIG. 5A

| | |
|---|---|
| ('410','411','412','413','414') | 0.81551 |
| ('415','416','417') | -0.13910 |
| ('420','421','422','423','424','425','426','427','428','429') | 0.59479 |
| ('430','431','432','433','434','435','436','437','438') | 0.06671 |
| ('440','441','442','443','444','445','446','447','448') | 0.14306 |
| ('451','452','453','454','455','456','457','458','459') | 0.53461 |
| ('461') | 0.46493 |
| ('462') | 0.88908 |
| ('465') | 0.74045 |
| ('466') | 0.56349 |
| ('470','471','472','473','474','475','476','477','478') | 0.65094 |
| ('480','481','482','483','484','485','486','487') | 0.52782 |
| ('490','491','492','493','494','495','496') | 0.68342 |
| ('500','501','502','503','504','505','506','507','508') | -0.11220 |
| ('510','511','512','513','514','515','516','517','518','519') | 0.25934 |
| ('526','527','528','529') | 0.42699 |
| ('530','531','532','533','534','535','536','537') | 0.38621 |
| ('540','541','542','543') | 1.49692 |
| ('550','551','552','553') | 0.98055 |
| ('555','556','557','558') | 0.62535 |
| ('560','562','564','565','566','567','568','569') | 0.47733 |
| ('570','571','572','573','574','575','576','577','578','579') | 0.58122 |
| ('580','581','582','583','584','585','586','587','588','589') | 0.07132 |
| ('590','591','592','593','594','595','596','597','598','599') | 0.46404 |
| ('600','601','602','603','604','605','606','607','608') | 1.10284 |
| ('610','611') | 0.33865 |
| ('614','615','616) | 0.53492 |
| ('617','618','619','620','621','622','623','624','625','626','627','628','629') | 0.74930 |
| ('640','641','642','643','644','645','646','647','648') | 1.22210 |
| ('680','681','682','683','684','685','686') | 0.60087 |
| ('690','691','692','693','694','695','696','697','698') | 0.66122 |
| ('710','711','712','713','714','715','716','717','718','719') | 0.88132 |
| ('720','721','723','724') | 0.80489 |
| ('725','726','727','728','729') | 0.69042 |
| ('730','731','732','733','734','735','736','737','738','739') | 0.40566 |
| ('740','741','742','743','744','745','746','747','748','749','750','751','752','753','754','755','756','757','758','759') | 0.66376 |
| ('764','765','766','767','768','769','770','771','772','773','774','775','776','777','778','779') | 0.65475 |
| ('780','781','782','783','784','785','786','787','788','789') | 1.18758 |
| ('790','791','792','793','794','795','796') | 0.47375 |
| ('799') | 0.03047 |
| ('V07','V08','V09') | 0.71592 |
| ('V10','V11','V12','V13) | 0.29565 |
| ('V22') | 1.77525 |
| ('V23','V24','V27') | 0.74963 |
| ('V30','V31','V36','V37','V39') | 1.38693 |
| ('V41','V42','V43','V44','V45','V46','V47','V48','V49') | 0.46725 |
| ('V50','V52','V54','V55','V56','V57','V58') | 0.60718 |
| ('V67','V68') | 0.51610 |
| ('V70','V71','V72','V73','V74','V75','V76','V77','V78','V79','V80','V81','V82') | 1.60133 |

FIG. 5B

COMPUTER SYSTEM AND METHOD FOR GENERATING HEALTHCARE RISK INDICES USING MEDICAL CLAIMS INFORMATION

RELATED APPLICATIONS

This application is a continuation in part of U.S. patent application Ser. No. 10/689,852, filed Oct. 22, 2003, "Computer System and Method for Generating Healthcare Risk Indices Using Medication Compliance Information," which is assigned to the assignee of this application and is incorporated herein by reference.

BACKGROUND OF THE INVENTION

1. Field of the Invention

The present invention is directed to computer-related and/or assisted systems, methods, and computer program devices for facilitating efficient and effective healthcare management programs. More particularly, the present invention relates to techniques for generating a risk index which may be used for clinical case identification, such as e.g., disease management programs, to explain and predict variation in medical-related costs, and to explain and predict variation in total healthcare costs or utilization.

2. Description of the Related Art

A first major fact or first major economic problem that has surfaced during the past twenty years has been the upward spiraling cost of medical care. Demographic factors have played one role in this increased cost since extended life expectancies increase the percentage of older individuals in the population. Generally, such individuals require a much higher degree of medical care.

A second major fact or contributer to increased costs for medical care has been the advent of many new, expensive, medical procedures which have sprung from medical and instrumentation advances of the past ten years. More widely known examples are organ transplants and the use of CAT scanners or MRI units for routine diagnosis.

An additional factor resulting in these increased costs has been the increased rate of inflation, which has dramatically influenced the costs for drugs. Due to all of the above, as well as other factors, the cost of even routine medical care has increased dramatically.

Correspondingly, increasing numbers of healthcare studies have been commissioned with the stated goal of optimizing healthcare services and expenditures. For instance, numerous methods and techniques have been proposed, which attempt to increase healthcare efficiency by predicting healthcare costs.

For example, U.S. Pat. No. 4,667,292, issued to Mohlenbrock, et al., in 1987, and incorporated herein by reference, discloses a medical reimbursement computer system which generates a list identifying the most appropriate diagnostic-related group (DRG) and related categories applicable to a given patient for inpatient claims (see, e.g., STEPS 33-65 of Prior Art FIG. 3). The list is limited by a combination of the characteristics of the patient and an initial principal diagnosis. A physician can choose a new designation from a list of related categories while the patient is still being treated. Manually determined International Classification Diagnostic Code (ICD-9) numbers can then be applied to an available grouper computer program to compare the working DRG to the government's DRG. This information may be used in conjunction with predicting healthcare costs. ICD-9 diagnostic codes are standard codes used by physicians to identify the diagnostic procedure that was preformed on the patient, primarily for billing purposes for example, through a managed health care provider.

U.S. Pat. No. 5,018,067, also issued to Mohlenbrock, et al., in 1991, and incorporated herein by reference, discloses an apparatus and method for improved estimation of healthcare resource consumption through the use of diagnostic and/or procedure-grouping and severity of illness indicators. This system is a computer-implemented program that calculates the amount of payment to a health provider by extracting the same input data as that identified in the Mohlenbrock '292 patent (which discloses the DRG System). The system calculates the severity of the patient's illness then classifies each patient into sub-categories of resource consumption within a designated DRG. A computer combines the input data according to a formula consisting of constants and variables. The variables are known for each patient and relate to the number of ICD codes and the government weighing of the codes. The software program determines a set of constants for use in the formula for a given DRG which minimizes variances between the actual known outcomes and those estimated by use of the formula. Because it is based upon various levels of illness severity within each diagnosis, the results of this system provide a much more homogenous grouping of patients than is provided by the DRGS. Providers can be compared to each other to identify those providers whose practice patterns are of the highest quality and most cost efficient. A set of actual costs incurred can be compared with the estimated costs. After the initial diagnosis, the system determines the expected costs of treating a patient.

U.S. Pat. No. 5,325,293 to Dorne, issued in 1994, and incorporated herein by reference, discloses a system and method for correlating medical procedures and medical billing codes. After an examination, the system automatically determines raw codes directly associated with all of the medical procedures performed or planned to be performed with a particular patient. The system allows the physician to modify the procedures after performing the examination. By manipulating the raw codes, the system generates intermediate and billing codes without altering the raw codes.

While useful in their own ways, the techniques disclosed in the above-described prior art references, however, fail to meet all of the needs of today's healthcare community. For example, it has been determined by the inventors of the present invention that each of the techniques described above fail to consider the predictive nature of medical claims-based data (e.g., the ability to predict and explain variation in costs using claims data).

While some techniques use medical claims data to determine the risk of death of a patient, no existing techniques make use of empirical medical claims data to predict, e.g., healthcare costs.

Therefore, what is needed is a technique that predicts risk based on chronic conditions possessed by an individual patient as determined according to the individual's medical claims information.

SUMMARY OF THE INVENTION

The present invention is directed to generating a healthcare risk index using a patient's or individual's medical claims, which are indicative of, for example, chronic conditions possessed by the individual. The index may be used to explain and predict variation in medical-related costs and variation in total healthcare costs or utilization.

Various considerations and/or factors may be used in creating the healthcare risk index. One example of the method used to create the healthcare index includes first examining the individual's medical claims to identify any chronic conditions possessed by that individual. The chronic condition information is used to generate a chronic condition score by summing regression coefficients for each chronic condition possessed by the individual.

One embodiment of the present invention is now summarized. In particular, a healthcare risk index is generated using medical claims to estimate risk. More specifically, the healthcare risk index represents a medical claims-based co-morbidity risk index. The index was developed to allow accurate comparisons between various populations by adjusting for a "burden of illness." In addition, the index may be used to predict future medical costs, total healthcare costs, and probability and amounts of future medical services utilization.

In use, individual patients (e.g., members of a particular healthcare insurance plan) receive risk scores based on chronic conditions. Scores increase, for example, with the number of diseases present, with more costly diseases receiving higher scores. In one embodiment, the risk index was developed using patient information from a conventional medical claims database and from patient eligibility data. In other embodiments, other medical claims databases, along with patient eligibility information, may be utilized in conjunction with the present invention. For example, database information provided by any health insurer or pharmacy benefits manager may just as easily be utilized. In any event, scoring is based on values obtained from these data sources.

The uses of such a healthcare risk index are many. For example, the index may be used for research and actuarial purposes, such as clinical case identification uses (e.g., disease management programs). Similarly, the index may be used to explain and predict variation in medical-related costs and variation in total healthcare costs or utilization. Further, the index may be used as a tool in program evaluation to create comparable groups to adjust for factors such as adverse or favorable selection into healthplans, programs or health-related interventions.

Thus, the healthcare risk index of the present invention advantageously solves, for example, three problems: clinical case identification/disease management, prediction of concurrent and prospective medical-related and total healthcare costs, and allows the comparison of groups which may have differing rates of chronic illness.

According to other aspects of the present invention, empirical or actual medical claims data may be utilized to predict healthcare costs. In these embodiments, a healthcare risk index may be generated using a patient's or individual's medical claims, which may be indicative of, for example, chronic conditions possessed by the individual. Like the indices described above, this index may be used to explain and predict variation in medical-related costs and variation in total healthcare costs or utilization.

More specifically, the index, in some embodiments, may be described as a medical claims-based co-morbidity risk index. Plan members receive a "risk score" based on the chronic conditions that are present. Scores increase with the number of diseases present with more costly diseases receiving higher scores. In one exemplary embodiment, this co-morbidity risk index may be developed using any standard medical claims database.

The medical claims are reviewed to determine which conditions exist for each patient and indicator variables are set to 1 or TRUE if the condition exists. From there, regression coefficients may be multiplied by the indicator variables and summed to arrive at an index or score. Sample indicator weights or regression coefficients are shown in the table I below, using conditions labeled and grouped according to the International Classification Diagnostic Codes (ICD-9 Codes) instead of, and/or in addition to, for example, chronic conditions and/or compliance medications. Any combination of condition groupings may be utilized in generating the index.

TABLE I

| Conditions (3-digit ICD-9 codes) | Weights |
|---|---|
| ('001', '002', '003', '004', '005', '006', '007', '008', '009') | 0.51927 |
| ('010', '011', '012', '013', '014', '015', '016', '017', '018') | 0.67509 |
| ('020', '021', '022', '023', '024', '025', '026', '027') | 0.08939 |
| ('030', '031', '032', '033', '034', '035', '036', '037', '038', '039') | 0.62525 |
| ('042') | 2.69484 |
| ('040', '041', '043', '044', '045', '046', '047', '048', '049') | 0.41242 |
| ('060', '061', '062', '063', '064', '065', '066') | 0.80152 |
| ('080', '081', '082', '083', '084', '085', '086', '087', '088') | 0.71995 |
| ('090', '091', '092', '093', '094', '095', '096', '097', '098', '099') | 0.75938 |
| ('100', '101', '102', '103', '104') | 0.52743 |
| ('112') | 0.32795 |
| ('110', '111', '113', '114', '115', '116', '117', '118') | 0.40347 |
| ('120', '121', '122', '123', '124', '125', '126', '127', '128', '129') | 0.44208 |
| ('130', '131', '132', '133', '134', '135', '136' | 0.35877 |
| ('140', '141', '142', '143', '144', '145', '146', '147', '148', '149') | 0.24868 |
| ('150', '151', '152', '153', '154', '155', '156', '157', '158', '159') | 0.63380 |
| ('160', '161', '162', '163', '164', '165') | 0.27897 |
| ('170', '171', '182', '173', '174', '175', '176') | 0.57732 |
| ('179', '180', '181', '182', '183', '184', '185', '186', '187', '188', '189') | 0.89246 |
| ('190', '191', '192', '193', '194', '195', '196', '197', '198', '199') | 0.52960 |
| ('200', '201', '202', '203', '203', '205', '206', '207', '208') | 0.81431 |
| ('210', '211', '212', '213', '214', '215', '216', '217', '218', '219', '220', '221', '222', '223', '224', '225', '226', '227', '228', '229') | 0.74376 |
| ('230', '231', '232', '233', '234') | 0.32539 |
| ('235', '236', '237', '238') | 0.41101 |
| ('239') | 0.28258 |
| ('240', '241', '242', '243', '244', '245', '246') | 0.67404 |
| ('250') | 1.14089 |
| ('251', '251', '252', '253', '254', '255', '256', '257', '258', '259') | 0.62899 |
| ('260', '261', '262', '263', '264', '265', '266', '267', '268', '269') | 0.08597 |
| ('272') | 0.90419 |
| ('270', '271', '273', '274', '275', '276', '277', '278', '279') | 0.43509 |
| ('280', '281', '282', '283', '284', '285', '286', '287', '288', '288') | 0.47204 |
| ('290', '291', '292', '293', '294') | 0.24155 |

TABLE I-continued

| Conditions (3-digit ICD-9 codes) | Weights |
| --- | --- |
| ('296') | 0.64358 |
| ('295', '297', '298', '299') | 0.84728 |
| ('300') | 0.80920 |
| ('301', '303', '304', '305', '307', '309', '310', '311', '312', '313', '314', '315', '316') | 0.90559 |
| ('317', '318', '319') | 0.63410 |
| ('320', '321', '322', '323', '324', '325', '326') | 0.35817 |
| ('330', '331', '332', '333', '334', '335', '336', '337') | 0.25770 |
| ('340', '341', '342', '343', '344', '345', '346', '347', '348', '349') | 0.51194 |
| ('350', '351', '352', '353', '354', '355', '356', '357', '358', '359') | 0.30996 |
| ('362') | 0.49639 |
| ('365') | 0.56865 |
| ('366') | 0.43326 |
| ('372') | 0.58989 |
| ('360', '361', '363', '364', '367', '368', '369', '370', '371', '373', '374', '375', '376', '377', '378', '379') | 0.73834 |
| ('381') | 0.55835 |
| ('382') | 0.89834 |
| ('383') | 0.44642 |
| ('384', '385', '386', '387', '388', '389') | 0.38326 |
| ('390', '391', '392') | 0.75715 |
| ('393', '394', '395', '396', '397', '398') | 0.37887 |
| ('401', '402', '403', '404', '405') | 1.07218 |
| ('410', '411', '412', '413', '414') | 0.81551 |
| ('415', '416', '417') | −0.13910 |
| ('420', '421', '422', '423', '424', '425', '426', '427', '428', '429') | 0.59479 |
| ('430', '431', '432', '433', '434', '435', '436', '437', '438') | 0.06671 |
| ('440', '441', '442', '443', '444', '445', '446', '447', '448') | 0.14306 |
| ('451', '452', '453', '454', '455', '456', '457', '458', '459') | 0.53461 |
| ('461') | 0.46493 |
| ('462') | 0.88908 |
| ('465') | 0.74045 |
| ('466') | 0.56349 |
| ('470', '471', '472', '473', '474', '475', '476', '477', '478') | 0.65094 |
| ('480', '481', '482', '483', '484', '485', '486', '487') | 0.52782 |
| ('490', '491', '492', '493', '494', '495', '496') | 0.68342 |
| ('500', '501', '502', '503', '504', '505', '506', '507', '508') | −0.11220 |
| ('510', '511', '512', '513', '5104', '515', '516', '517', '518', '519') | 0.25934 |
| ('526', '527', '528', '529') | 0.42699 |
| ('530', '531', '532', '533', '534', '535', '536', '537') | 0.38621 |
| ('540', '541', '542', '543') | 1.49692 |
| ('550', '551', '552', '553') | 0.98055 |
| ('555', '556', '557', '558') | 0.62535 |
| ('560', '562', '564', '565', '566', '567', '568', '569') | 0.47733 |
| ('570', '571', '572', '573', '574', '575', '576', '577', '578', '579') | 0.58122 |
| ('580', '581', '582', '583', '584', '585', '586', '587', '588', '589') | 0.07132 |
| ('590', '591', '592', '593', '594', '595', '596', '597', '598', '599') | 0.46404 |
| ('600', '601', '602', '603', '604', '605', '606', '607', '608') | 1.10284 |
| ('610', '611') | 0.33865 |
| ('614', '615', '616') | 0.53492 |
| ('617', '618', '619', '620', '621', '622', '623', '624', '625', '626', '627', '628', '629') | 0.74930 |
| ('640', '641', '642', '643', '644', '645', '646', '647', '648') | 1.22210 |
| ('680', '681', '682', '683', '684', '685', '686') | 0.60087 |
| ('690', '691', '692', '693', '694', '695', '696', '697', '698') | 0.66122 |
| ('710', '711', '712', '713', '714', '715', '716', '717', '718', '719') | 0.88132 |
| ('720', '721', '723', '724') | 0.80489 |
| ('725', '726', '727', '728', '729') | 0.69042 |
| ('730', '731', '732', '733', '734', '735', '736', '737', '738', '739') | 0.40566 |
| ('740', '741', '742', '743', '744', '745', '746', '747', '748', '749', '750', '751', '752', '753', '754', '755', '756', '757', '758', '759') | 0.66376 |
| ('764', '765', '766', '767', '768', '769', '770', '771', '772', '773', '774', '775', '776', '777', '778', '779') | 0.65475 |
| ('780', '781', '782', '783', '784', '785', '786', '787', '788', '789') | 1.18758 |
| ('790', '791', '792', '793', '794', '795', '796') | 0.47375 |
| ('799') | 0.03047 |
| ('V07', 'V08', 'V09') | 0.71592 |
| ('V10', 'V11', 'V12', 'V13') | 0.29565 |
| ('V22') | 1.77525 |
| ('V23', 'V24', 'V27') | 0.74963 |
| ('V30', 'V31', 'V36', 'V37', 'V39') | 1.38693 |
| ('V41', 'V42', 'V43', 'V44', 'V45', 'V46', 'V48', 'V49') | 0.46725 |
| ('V50', 'V52', 'V54', 'V55', 'V56', 'V57', 'V58') | 0.60718 |
| ('V67', 'V68') | 0.51610 |
| ('V70', 'V71', 'V72', 'V73', 'V74', 'V75', 'V76', 'V77', 'V78', 'V79', 'V80', 'V81', 'V82') | 1.60133 |

One example of such a method involves first generating a medical condition score using the individual's medical information for each medical condition possessed by the individual. From there, each medical condition score is modified according to a regression coefficient, to result in one or more modified medical condition scores. Finally, the risk index may be generated by summing the medical condition scores. This risk index is indicative of at least one of the individual's medical costs, chronic medical conditions, and variation in medical costs.

The original invention alleviates the deficiencies of the conventional techniques and systems described above in the various alternate embodiments described herein. Specifically, a healthcare risk index is generated using a patient or individual's pharmacy claims, which are indicative of, for example, chronic conditions possessed by the individual, the individual's compliance on certain medications, and situations where the individual has no pharmacy claims whatsoever. The index may be used to explain and predict variation in pharmacy-related costs and variation in total healthcare costs or utilization.

Various considerations and/or factors may be used in creating the healthcare risk index. One example of the method used to create the healthcare index includes first examining the individual's pharmacy claims to identify any chronic conditions possessed by that individual. Similarly, the individual's pharmacy claims are examined to identify any compliance medications prescribed to the individual. The chronic condition information is used to generate a chronic condition score by summing regression coefficients for each chronic condition possessed by the individual. Likewise, the compliance medication information is used to generate a compliance medication score by summing products of regression coefficients for each compliance medication prescribed to the individual with associated medication supply weights. From there, a modified chronic condition score is generated by multiplying the chronic condition score by an overall chronic condition regression coefficient. The modified chronic condition score may then be further modified by subtracting a no-claims weight from the chronic condition score in cases where the individual has no pharmacy claims. Finally, the risk index may be determined by summing the modified chronic condition score and the compliance medication score. Any variation of the above method may alternatively be used that considers similar, additional and/or other factors in determining the healthcare risk index.

One embodiment of the original invention is now summarized. In particular, a compliance-based risk index is generated using pharmacy claims to estimate risk. More specifically, the compliance-based risk index represents a pharmacy claims-based co-morbidity risk index. The index was developed to allow accurate comparisons between various populations by adjusting for a "burden of illness." In addition, the index may be used to predict future medical costs, total healthcare costs, and probability and amounts of future medical services utilization.

In use, individual patients (e.g., members of a particular healthcare insurance plan) receive risk scores based on chronic medications used, as well as their is compliance on those medications. Scores increase, for example, with the number of diseases present, with more costly diseases receiving higher scores. In addition, plan members with non-chronic acute medication use are distinguished from those with no utilization. In one embodiment, the risk index was developed using patient information from a conventional pharmacy claims database and from patient eligibility data. In other embodiments, other pharmacy claims databases, along with patient eligibility information, may be utilized in conjunction with the original invention. For example, database information provided by any health insurer or pharmacy benefits manager may just as easily be utilized. In any event, scoring is based on values obtained from these data sources.

The uses of such a compliance-based risk index are many. For example, the index may be used for research and actuarial purposes, such as clinical case identification uses (e.g., disease management programs). Similarly, the index may be used to explain and predict variation in pharmacy-related costs and variation in total healthcare costs or utilization. Further, the index may be used as a tool in program evaluation to create comparable groups to adjust for factors such as adverse or favorable selection into healthplans, programs or health-related interventions.

Thus, the compliance-based risk index of the original invention advantageously solves, for example, three problems: clinical case identification/disease management, prediction of concurrent and prospective pharmacy-related and total healthcare costs, and allows the comparison of groups which may have differing rates of chronic illness.

The probability sample, which in one embodiment is a pharmacy claims database, was used to develop the index. More particularly, the pharmacy claims from the data source are first reviewed to determine which conditions exist for each patient and indicator variables are set if the conditions exist. Sample chronic conditions indicator weights are provided in the table below.

| Category | Chronic Conditions | Weights |
| --- | --- | --- |
| XA | Acid Peptic Disorders | 10.3039 |
| XB | Treatment for acne | 10.6623 |
| XC | Attention Deficit/Hyperactivity Disorder (under 18) | 13.9197 |
| XD | Advanced Liver Disease | 0.54999 |
| XE | AIDS | 31.9221 |
| XF | Allergic Rhinitis | 10.1509 |
| XG | Amyotrophic Lateral Schlerosis (Lou Gehrig's disease) | 29.0981 |
| XH | Alzheimer's Disease | 6.54956 |
| XI | Angina/Coronary Artery Disease | 0.067019 |
| XJ | Anxiety Disorder/Panic Disorder/Social Phobia | 3.17593 |
| XK | Arrythmia | 6.09765 |
| XL | Asthma (under 55) | 9.0274 |
| XM | Benign Prostatic Hyperplasia | 7.97429 |
| XN | Cancer (any type) | 10.8211 |
| XO | Congestive Heart Failure | 2.18044 |
| XP | Chronic Obstructive Pulmonary Disease (55+) | 3.57019 |
| XQ | Cystic Fibrosis | 5.16423 |
| XR | Depression | 10.3768 |
| XS | Diabetes Type I - Insulin dependent | 9.019 |
| XT | Diabetes Type II - Non-Insulin dependent | 7.29497 |
| XU | End Stage Renal Disease (ESRD) | 12.5402 |
| XV | Epilepsy | 6.93106 |
| XW | Gaucher's Disease | 83.2477 |
| XX | Glaucoma | 2.31705 |
| XY | Gout | 1.98149 |
| XZ | Growth Hormone Deficiency | 32.512 |
| XAA | Hepatitis B | 4.09929 |
| XBB | Hepatitis C | 33.2874 |
| XCC | High Cholesterol/Triglycerides | 10.7383 |
| XDD | Hypertension | 8.30913 |
| XEE | Hypothyroidism | 1.21422 |
| XFF | Inflammatory Bowel Disease | 8.56743 |
| XGG | Manic Depressive | 4.62228 |
| XHH | Migraine | 8.26695 |
| XLL | Multiple Sclerosis | 30.5853 |
| XMM | Organ Transplantation | 17.0153 |
| XNN | Menopause (Hormone Replacement Therapy) (45-59) | 7.26419 |

-continued

| Category | Chronic Conditions | Weights |
|---|---|---|
| XOO1 | Osteoporosis (Bone Resorption Suppression Agents) (60+) | 6.69366 |
| XOO2 | Osteoporosis (Estrogenic Agents) (60+) | 3.50463 |
| XPP | Parkinson's Disease | 8.11787 |
| XQQ | Peripheral Vascular Disease | 1.76236 |
| XRR | Psoriasis | 9.92265 |
| XSS | Psychotic Disorders/Dementia and no antidepressants (65+) | 4.5396 |
| XTT | Rheumatoid Arthritis | 10.5781 |
| XUU | Schizophrenia (under 65) | 13.8768 |
| XVV | Smoking Cessation | 3.40704 |
| XWW | Thromboembolytic Disease I (Platelet Aggregation Inhibitors) | 1.44029 |
| XKK | Thromboembolytic Disease II (Oral Anticoagulants, Coumarin Type) | 2.83761 |
| XYY | Tuberculosis | 5.049 |
| XZZ | Urinary Incontinence | 3.66661 |

The weights are then, for example, multiplied by the indicator variables (e.g., "1" for "TRUE" or the presence of the chronic condition and "0" for "FALSE" or the absence of the chronic condition) and, for example, summed to get a chronic conditions score. Furthermore, an indicator for patients with no pharmacy claims (e.g., a "no-claim" weight) may optionally be considered (set to a value of 1 for members with no pharmacy claims and 0 otherwise, which is multiplied by a no-claims weight) to further modify the chronic conditions score. Thus, this no-claim weight further emphasizes situations where an individual has no pharmacy claims whatsoever (i.e., the patient has no chronic condition claims, prescribed medications and/or other claims).

The pharmacy claims are also reviewed to determine compliance on certain pharmaceuticals of interest. In one embodiment, compliance is defined as the total days of supply over a year (e.g., the days supply divided by 365 times 100%). In other embodiments, other time periods are used (e.g., 7 days, 30 days, etc.). Two sets of weights, one from a log transform and one from a square-root transform are included in the table below, for each medication, for use in generating a compliance medication score. Either weight may be used. When the weights are developed in practice, in some cases, whichever transform minimizes the multiple regression model's error sum of squares may be most appropriate. The weights are multiplied by the indicator or numeric variables (i.e., the days supply or compliance) and summed to generate the medication compliance score.

| Compliance Medication | Weights for log index | Weights for square root index |
|---|---|---|
| Chronic Condition Score | 0.08036 | 0.65876 |
| No Claim | −2.24249 | −5.42877 |
| Asthma Medications | 0.00734 | 0.07566 |
| Asthma Controllers | 0.00246 | 0.06420 |
| Congestive Heart Failure Medications | −0.00095396 | 0.00615 |
| Angiotension Converting Enzymes | 0.00183 | 0.00987 |
| Gastrointestinal Medications | −0.00041974 | 0.04681 |
| Proton Pump Inhibitors | 0.00490 | 0.07727 |
| High Cholesterol Medications | 0.00020414 | 0.01141 |
| Statins | 0.00339 | 0.04491 |
| Diabetes Medications | −0.00010360 | 0.07623 |
| Diabetes Type 2 Medications | 0.00285 | 0.06342 |
| Depression Medications | 0.00358 | 0.07158 |
| Hypertension Medications | 0.00811 | 0.04302 |

Once generated, the medication compliance score and the chronic conditions score are summed to produce the risk index of the original invention, which (as mentioned above) may be used to predict future medical costs, total healthcare costs, and probability and amounts of future medical services utilization. Specifically, an individual with a higher score will likely have more comorbidities, and hence represent a more expensive patient, than an individual with a lower score. Thus, the risk indices of the individuals in a particular population may be compared, with higher scores indicating a high risk of pharmaceutical cost and risk of future total medical cost and medical utilization.

Hence, to achieve the above-stated goals and to address the above and other problems of the prior art, the original invention provides a method, system, and computer-readable instructions for generating a risk index for an individual using the individual's pharmacy claims. In at least one embodiment, the index is generated by first examining the individual's pharmacy claims to identify any predetermined conditions, such as chronic conditions possessed by the individual. Similarly, the individual's pharmacy claims are examined to identify any compliance medications prescribed to the individual. The chronic condition information is used, for example, to generate a chronic condition score by summing regression coefficients for each chronic condition possessed by the individual. Likewise, the compliance medication information is used, for example, to generate a compliance medication score by, for example, summing products of regression coefficients for each compliance medication prescribed to the individual with associated medication supply weights. From there, a modified chronic condition score is generated by, for example, multiplying the chronic condition score by a chronic condition regression coefficient. The modified chronic condition score may then be further modified by, for example, subtracting a no-claims weight from the chronic condition score in cases where the individual has no pharmacy claims. Finally, the risk index may be determined by, for example, summing the modified chronic condition score and the compliance medication score.

Other embodiments of the original invention also provide a method, system, and computer-readable instructions for generating a risk index for an individual using the individual's pharmacy claims. In these alternate embodiments, the index is generated by first generating a raw risk index indicative of at least one of the individual's raw relative medical costs, acute medical conditions, and variation in medical costs, by using the individual's pharmacy claims. Next, the raw risk index is modified in accordance with a compliance medication score, which is indicative of the individual's compliance with prescribed pharmaceuticals. Summing the above values results in the risk index of this embodiment of the original invention.

In yet other cases, other embodiments of the original invention provide method, system, and computer-readable instructions for generating a risk index for an individual using the individual's pharmacy claims and a no-claims weight. In these alternate embodiments, the index is generated by first generating a raw risk index indicative of at least one of the individual's raw relative medical costs, acute medical conditions, and variation in medical costs, by using the individual's pharmacy claims. Subsequently, the raw risk index is modified in accordance with a no-claims weight, which is indicative of an absence of claims in the individual's pharmacy claims. Like the above, summing these values results in the risk index of this embodiment of the original invention.

According to other aspects of the original invention, empirical or actual medical claims data may be utilized to predict healthcare costs. In these embodiments, a healthcare risk index may be generated using a patient's or individual's medical claims, which may be indicative of, for example, chronic conditions possessed by the individual. Like the indices described above, this index may be used to explain and predict variation in pharmacy-related costs and variation in total healthcare costs or utilization.

More specifically, the index, in some embodiments, may be described as a medical claims-based co-morbidity risk index. Plan members receive a "risk score" based on the chronic conditions that are present. Scores increase with the number of diseases present with more costly diseases receiving higher scores. In one exemplary embodiment, this co-morbidity risk index may be developed using any standard medical claims database.

The medical claims-based co-morbidity risk index and the pharmacy claims-based co-morbidity risk index may be used alone or together to advantageously solve, for example, three problems: clinical case identification/disease management, prediction of concurrent and prospective medical-related, pharmacy-related and total healthcare costs or utilization, and the comparison of groups which may have differing rates of chronic illness. Although these indices can be slightly correlated, including them both in models built for the above purposes, reduces the error variance (noise) in the data and leads to better estimates and tests.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE SEVERAL VIEWS OF THE DRAWING(S)

The above-mentioned and other advantages and features of the present invention will be better understood from the following detailed description of the invention with FIG. 1 is a block diagram example of a computer utilizable for generating the risk index of the present invention;

FIGS. 5A and 5B lists examples of chronic conditions and associated regression coefficients utilizable in generating the risk index described in FIG. 4.

DETAILED DESCRIPTION OF THE INVENTION

The following detailed description includes many specific details. The inclusion of such details is for the purpose of illustration only and should not be understood to limit the invention. Throughout this discussion, similar elements are referred to by similar numbers in the various figures for ease of reference. In addition, features in one embodiment may be combined with features in other embodiments of the invention.

Specifically, a healthcare risk index is generated using, for example, information from a patient or individual's medical claims, which are indicative of, for example, chronic conditions possessed by the individual. The index may be used to explain and predict variation in medical-related costs and variation in total healthcare costs or utilization. In particular, the index is generated, for example, by first examining the individual's medical claims to identify any chronic conditions possessed by the individual. The chronic condition information is used, for example, to generate a chronic condition score by summing regression coefficients for each chronic condition possessed by the individual.

Figure 4:
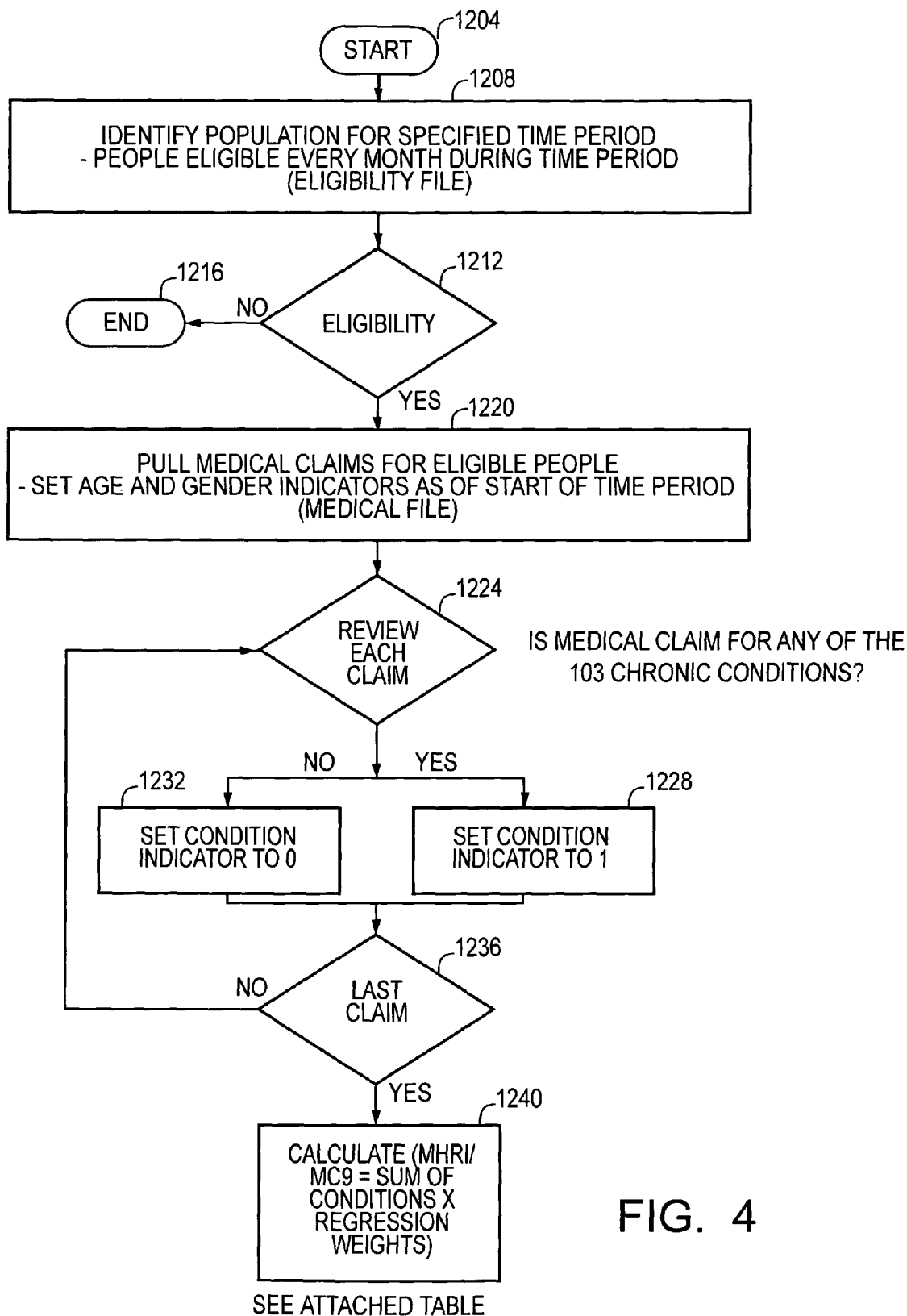
FIG. 4 is one example of a process which utilizes medical condition information for generating a risk index according to the techniques of the present invention.

As mentioned above, embodiments of the present invention contemplate using medical claims information for generating a risk index. Referring to FIG. 4, one example of a process utilizable for generating a medical claims risk index, according to the techniques of the present invention, is illustrated. As with the above embodiments, the risk index of this embodiment also represents a "burden of illness" score, which when compared to other scores, may be used to predict relative healthcare costs.

In accordance with the concepts of the present invention, numerous factors may affect the risk index. For example, the scores may increase according to the number of diseases present. In particular, some embodiments may consider the presence or absence of any combination of the conditions covered by the International Classification Diagnostics Code (ICD-9 Codes). For example, standard groupings of three digit codes representing a category of disease conditions may be used. Disease conditions that coincide with the codes can be found in the Integrated Classification of Diseases (ICD-9-CM) book published by the American Medical Association, incorporated herein by reference. The codes were combined to create categories of conditions based on this book. For instance, 001-009 represent intestinal infectious diseases, and 010-018 represent tuberculosis, etc. Thus, some embodiments may include regression coefficients corresponding to chronic conditions to determine the risk index for an individual or group of individuals.

The generation of the risk index commences (STEP 1204) with the determination of an eligible population for a specified period of time (STEP 1208). To perform this step, the process may examine the contents of an eligibility file. In most cases, the eligibility file includes a database containing a list of each of the eligible individuals, maintained by a managed care organization, a pharmacy benefits manager, a human resources department of an employer, or other similar organization. For example, the eligible individuals may include each of those employees of a particular employer that have elected to receive healthcare benefits from the employer. In contrast, individuals that have elected not to receive healthcare benefits from the employer constitute ineligible individuals.

Thus, the process examines each entry or individual for eligibility (STEP 1212). For each ineligible individual, processing terminates (STEP 1216), with no risk score being generated for that individual. For those that are eligible, medical claims information for the individuals are examined (STEP 120).

For example, a medical file, which is used to maintain the medical history data for each of the individuals, is retrieved and subsequently consulted. In addition to the patient's name, gender, age, and other personal information, this file includes information describing each chronic condition possessed by the individual. For example, the data may include hospitalizations or physician office visits that are covered under a benefit offer by the employer. As such, this information may be used to determine which conditions are possessed.

Once the medical claims information for the eligible individuals has been retrieved, the data for each individual is reviewed (STEP 1224). As a result, the process identifies each of the chronic conditions of issue possessed by the individual.

In accordance with the concepts of the present invention, with each condition possessed by an individual, a condition indicator for that condition is set to "1" or "TRUE" (STEP 1228). With individuals determined not to have the condition, the condition indicator may be set to "0" or "FALSE" (STEP 1232).

In some embodiments, to determine the presence or absence of a condition, the medical claims may be searched for a predetermined number of chronic conditions or diseases. Furthermore, the exact combination of chronic conditions may be determined by the administrator or user of the system. This process continues until the data has been examined for each of the conditions of interest (STEP 1236).

Once the list of conditions present have been determined, a medical condition score may be generated. The general formula is cost=condition$_1$weight×condition$_1$+ . . . +condition$_n$weight×condition$_n$, where condition$_1$ through condition$_n$ are indicator variables that are equal to 1 if the condition exists.

In the example illustrated in FIG. 4, this score is generated by summing weights associated with each condition possessed by the individual. Specifically, for each chronic condition possessed by an individual, a weight associated with the condition is added to or summed with the medical condition score (STEP 1240). As an example, the weights listed in the table of FIGS. 5A and 5B may be used. Thus, a chronic condition score associated with a patient diagnosed with diabetes (identified by ICD-9 code '250') is increased by the weight associated with diabetes, which in this case is 1.14089. Similarly, if that same patient also has affective psychoses including depression (identified by ICD-9 code '296'), the chronic condition score is increased by an additional 0.64358. The sum total of these chronic condition weights thereby constitutes the medical condition score of an individual. In the example above, the medical condition score would be 1.14089+0.64358=1.78447. The weights associated with the medical conditions are generated using information contained in a medical claims database. Specifically, each weight represents the regression coefficient developed using a multiple regression model with medical or total cost as the dependent variable and all chronic conditions of interest as independent variables. The coefficients shown in the example of FIGS. 5A and 5B were determined using data from a medical benefits manager database. Data sources (such as other health insurers, PBMs medical claims, etc.) may be utilized by those of ordinary skill in the art to calculate these regression coefficients. Other methods of determining a score qualitatively representative of the chronic condition may alternatively be used.

Figure 1:
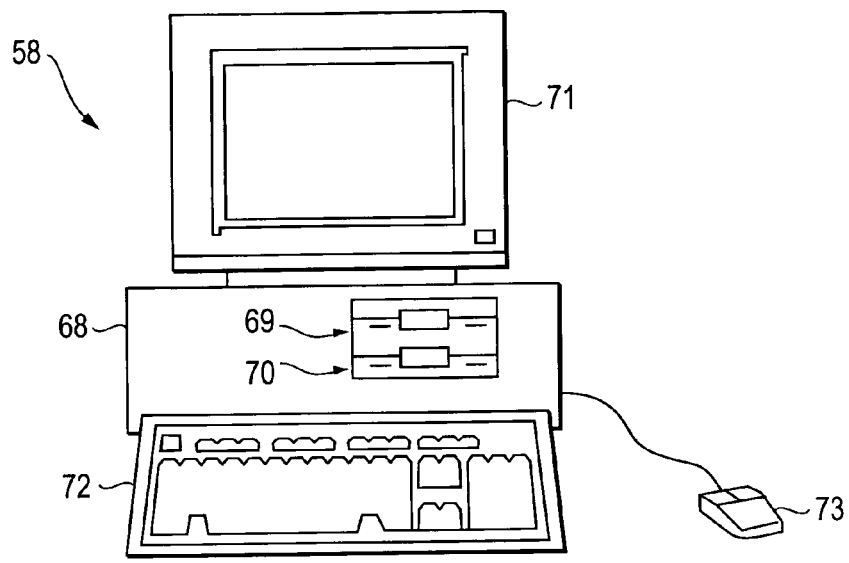

The risk index generation process of the present invention may be implemented in any computer system or computer-based controller. One example of such a system is described in greater detail below with reference to FIG. 1. More specifically, FIG. 1 is an illustration of a computer 58 used for implementing the computer processing in accordance with a computer-implemented embodiment of the present invention. The procedures described above may be presented in terms of program procedures executed on, for example, a computer or network of computers, including local and/or global area networks such as the Internet.

Viewed externally in FIG. 1, computer 58 has a central processing unit (CPU) 68 having disk drives 69, 70. Disk drives 69, 70 are merely symbolic of a number of disk drives that might be accommodated by computer 58. Typically, these might be one or more of the following: a floppy disk drive 69, a hard disk drive (not shown), and a CD ROM or digital video disk, as indicated by the slot at 70. The number and type of drives varies, typically with different computer configurations. Disk drives 69, 70 are, in fact, options, and for space considerations, may be omitted from the computer system used in conjunction with the processes described herein.

Computer 58 also has a display 71 upon which information may be displayed. The display is optional for the computer used in conjunction with the system described herein. A keyboard 72 and/or a pointing device 73, such as a mouse 73, may be provided as input devices to interface with central processing unit 68. To increase input efficiency, keyboard 72 may be supplemented or replaced with a scanner, card reader, or other data input device. The pointing device 73 may be a mouse, touch pad control device, track ball device, or any other type of pointing device.

Figure 2:
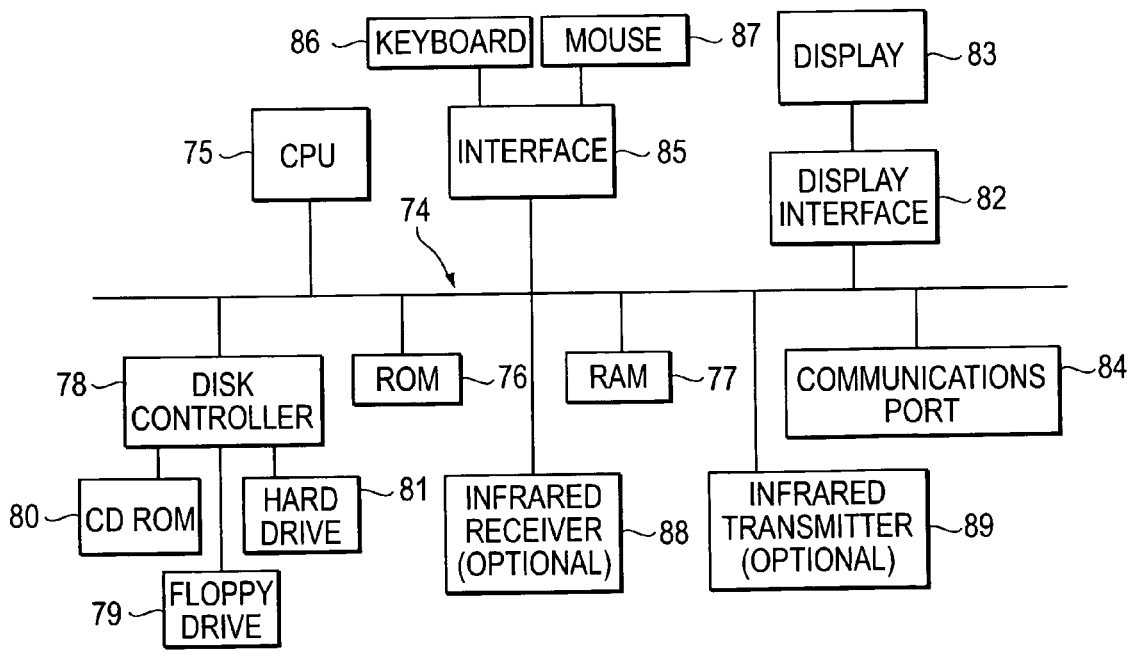
FIG. 2 illustrates a block diagram of the internal hardware of the computer of FIG. 1.
Figure 3:
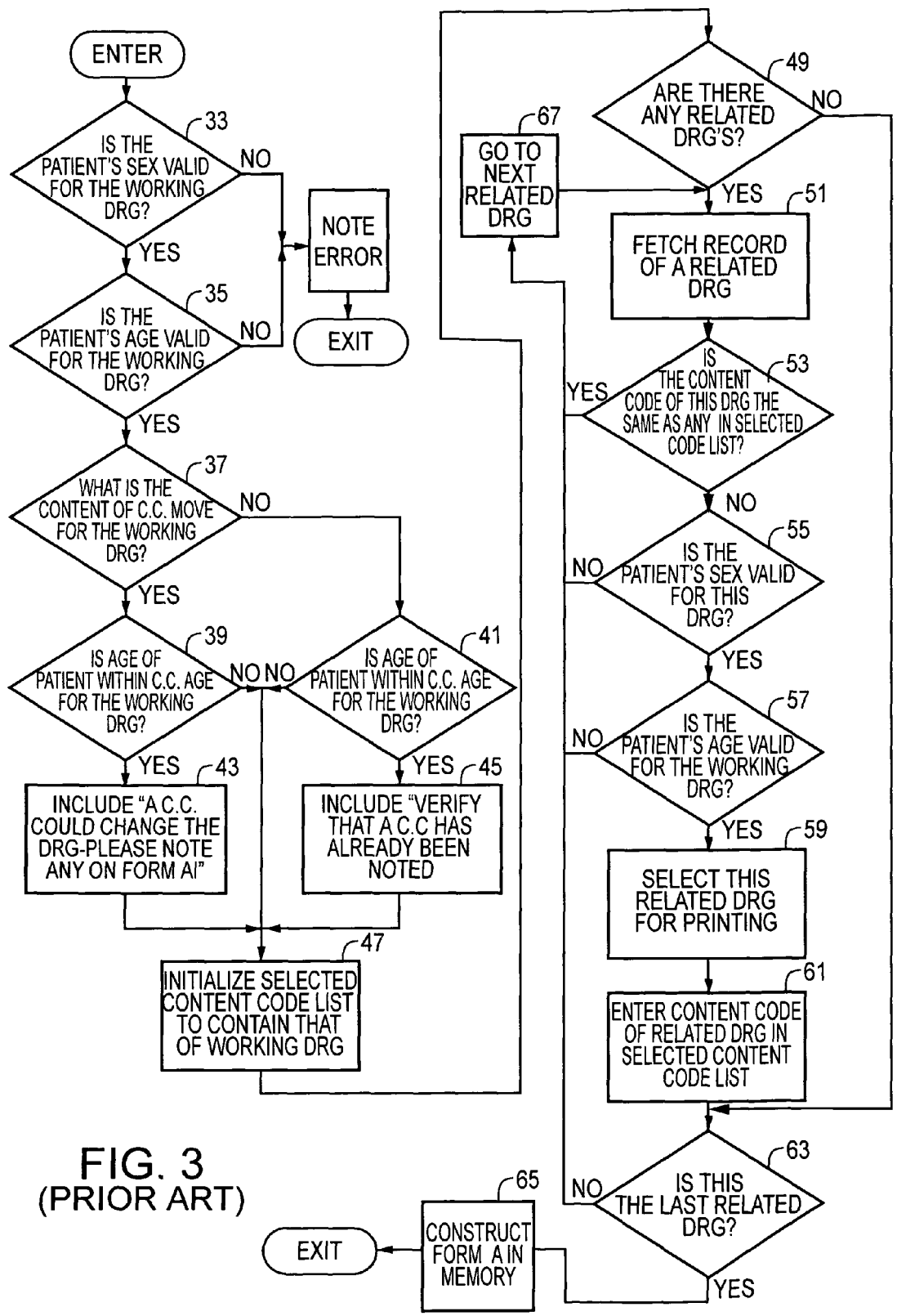
FIG. 3 depicts a prior art method used to implement a medical reimbursement computer program.

Alternatively, referring to FIG. 2, computer 58 may also include a CD ROM reader and writer 80, which are interconnected by a bus 74 along with other peripheral devices supported by the bus structure and protocol. Bus 74 serves as the main information highway interconnecting other components of the computer.

FIG. 2 illustrates a block diagram of the internal hardware of the computer of FIG. 1. CPU 75 is the central processing unit of the system, performing calculations and logic operations required to execute a program. Read only memory (ROM) 76 and random access memory (RAM) 77 constitute the main memory of the computer. Disk controller 78 interfaces one or more disk drives to the system bus 74. These disk drives may be floppy disk drives such as 79, or CD ROM or DVD (digital video/versatile disk) drives, as at 80, or internal or external hard drives 81. As previously indicated these various disk drives and disk controllers are optional devices.

A display interface 82 permits information from bus 74 to be displayed on the display 83. Again, as indicated, the display 83 is an optional accessory for a central or remote computer in the communication network, as are infrared receiver 88 and transmitter 89. Communication with external devices occurs using communications port 84.

In addition to the standard components of the computer, the computer may also include an interface 85, which allows for data input through the keyboard 86 or pointing device, such as a mouse 87.

The foregoing detailed description includes many specific details. The inclusion of such detail is for the purpose of illustration only and should not be understood to limit the invention. In addition, features in one embodiment may be combined with features in other embodiments of the invention. Various changes may be made without departing from the scope of the invention as defined in the following claims.

As another example, the system according to the invention may include a general purpose computer, or a specially programmed special purpose computer. The user may interact with the system via e.g., a personal computer or over PDA, e.g., the Internet an Intranet, etc. Either of these may be implemented as a distributed computer system rather than a single computer. Similarly, the communications link may be a dedicated link, a modem over a POTS line, and/or any other method of communicating between computers and/or users. Moreover, the processing could be controlled by a software program on one or more computer systems or processors, or could even be partially or wholly implemented in hardware.

Although the computer system in FIG. 1 is illustrated as having a single computer, the system according to one or more embodiments of the invention is optionally suitably equipped with a multitude or combination of processors or storage devices. For example, the computer may be replaced by, or combined with, any suitable processing system operative in accordance with the concepts of embodiments of the present invention, including sophisticated calculators, hand held, laptop/notebook, mini, mainframe and super computers, as well as processing system network combinations of the same. Further, portions of the system may be provided in any appropriate electronic format, including, for example, provided over a communication line as electronic signals, provided on floppy disk, provided on CD Rom, provided on optical disk memory, etc.

Any presently available or future developed computer software language and/or hardware components can be employed in such embodiments of the present invention. For example, at least some of the functionality mentioned above could be implemented using Visual Basic, C, C++ or any assembly language appropriate in view of the processor being used. It could also be written in an interpretive environment such as Java and transported to multiple destinations to various users.

The many features and advantages of the embodiments of the present invention are apparent from the detail specification, and thus, it is intended by the appended claims to cover all such features and advantages of the invention that fall within the true spirit and scope of the invention. Further, since numerous modifications and variations were readily occurred to those skilled in the art, it is not desired to limit the invention to the exact construction and operation illustrated and described, and accordingly, all suitable modifications and equivalents maybe resorted to, falling within the scope of the invention.

What is claimed is:

1. A method comprising:
    determining, on a processor, in accordance with medical information of an individual, a first medical condition indicator value reflecting that the individual has a first medical condition, and a second medical condition indicator value reflecting that the individual does not have a second medical condition;
    calculating, on the processor, a first medical condition score by using the first medical condition indicator value and a first regression coefficient;
    calculating, on the processor, a second medical condition score by using the second medical condition indicator value and a second regression coefficient;
    identifying, on the processor, a compliance medication taken by the individual based on analysis of a plurality of pharmacy claims associated with the individual;
    calculating, on the processor, a compliance medication score for the compliance medication taken by the individual based on a determination of compliance by the individual with a treatment regimen and a compliance medication weight associated with a medication class type of the compliance medication;
    calculating, on the processor, a risk index by summing the first medical condition score, the second medical condition score, and the compliance medication score, the risk index being indicative of medical costs of the individual, chronic medical conditions, variation in medical costs, or combinations thereof based on the first medical condition that is indicated as possessed by the individual and the second medical condition that is indicated as not being possessed by the individual; and
    analyzing, on the processor, the risk index to determine a clinical case identification, disease management, prediction of concurrent and prospective medical related utilization, prediction of concurrent and prospective pharmacy-related utilization, prediction of concurrent and prospective total healthcare utilization, comparison of groups which may have differing rates of chronic illness, or combinations thereof.

2. The method of claim 1, wherein the first regression coefficient and the second regression coefficient are generated from a log transform.

3. The method of claim 1, wherein the first regression coefficient and the second regression coefficient are generated from a square-root transform.

4. The method of claim 1, wherein the medical information is obtained from a database managed by a managed care organization, a pharmacy benefits manager, a human resource department, or combinations thereof.

5. The method of claim 1, wherein the first medical condition score and the second medical condition score are determined responsive to an absence or presence of conditions identified by the International Classification Diagnostic Code (ICD-9).

6. The method of claim 1, wherein the medical information includes hospitalization visits information, physician office visits information, or both hospitalization visits information and physician office visits information.

7. The method of claim 1, wherein the determination of the risk index is limited to an eligible population.

8. The method of claim 7, wherein the eligible population is maintained by a managed care organization, a pharmacy benefits manager, a human resources department of an employer, or combinations thereof.

9. The method of claim 1, wherein the first regression coefficient is developed using a multiple regression model with at least one of a medical cost, a total cost, or both the medical cost and the total cost as the dependent variable and any chronic conditions of interest as the independent variable.

10. A non-transitory computer readable medium, which when executed by one or more processors, cause the one or more processors to perform the following operations:
    determine, in accordance with medical information of an individual, a first medical condition indicator value reflecting that the individual has a first medical condition, and a second medical condition indicator value reflecting that the individual does not have a second medical condition;

calculate a first medical condition score by using the first medical condition indicator value and a first regression coefficient;

calculate a second medical condition score by using the second medical condition indicator value and a second regression coefficient;

identify a compliance medication taken by the individual based on analysis of a plurality of pharmacy claims associated with the individual;

calculate a compliance medication score for the compliance medication taken by the individual based on a determination of compliance by the individual with a treatment regimen and a compliance medication weight associated with a medication class type of the compliance medication;

calculate a risk index by summing the first medical condition score, the second medical condition score, and the compliance medication score, the risk index being indicative of medical costs of the individual, chronic medical conditions, variation in medical costs, or combinations thereof based on the first medical condition that is indicated as possessed by the individual and the second medical condition that is indicated as not being possessed by the individual and analyze the risk index to determine a clinical case identification, disease management, prediction of concurrent and prospective medical related utilization, prediction of concurrent and prospective pharmacy-related utilization, prediction of concurrent and prospective total healthcare utilization, comparison of groups which may have differing rates of chronic illness, or combinations thereof.

11. The method of claim 1, wherein the first medical condition score is a first chronic medical condition score and the second medical condition score is a second chronic medical condition score.

12. The method of claim 1, wherein, the first regression coefficient and the second regression coefficient being developed from a multiple regression model with medical or total cost as a dependent variable and all chronic conditions of interest as independent variables.

\* \* \* \* \*